United States Patent [19]

Whitman

[11] Patent Number: 5,214,212
[45] Date of Patent: May 25, 1993

[54] PROMOTERS FOR HYDROGENATION OF AROMATIC AMINES

[75] Inventor: Peter J. Whitman, Hamden, Conn.

[73] Assignee: Olin Corporation, Cheshire, Conn.

[21] Appl. No.: 842,822

[22] Filed: Feb. 27, 1992

[51] Int. Cl.$^5$ .......................................... C07C 209/72
[52] U.S. Cl. ........................... 564/451; 564/450; 564/457; 564/461; 564/462
[58] Field of Search ............... 564/450, 451, 457, 461, 564/462

[56] References Cited

U.S. PATENT DOCUMENTS

| | | | |
|---|---|---|---|
| 1,862,599 | 6/1932 | Lommel | 564/450 |
| 1,927,129 | 9/1933 | Lommel | 564/450 |
| 2,166,971 | 7/1939 | Schmidt et al. | 564/450 |
| 2,511,028 | 6/1950 | Whitman | 564/451 |
| 2,606,924 | 8/1952 | Whitman | 260/563 |
| 2,606,925 | 8/1952 | Whitman | 260/563 |
| 2,606,928 | 8/1952 | Barkdoll et al. | 260/563 |
| 3,117,992 | 1/1964 | Duggan | 564/450 |
| 3,155,724 | 11/1964 | Arthur | 260/563 |
| 3,244,644 | 4/1966 | Stiles | 564/450 |
| 3,347,917 | 10/1967 | Arthur | 260/563 |
| 3,644,522 | 2/1972 | Brake et al. | 260/563 D |
| 3,679,746 | 7/1972 | Brake | 260/563 R |
| 3,697,449 | 10/1972 | Brake | 252/474 |
| 3,711,550 | 1/1973 | Brake | 260/563 B |
| 3,766,272 | 10/1973 | Brake | 260/563 B |
| 3,856,862 | 12/1974 | Chung et al. | 260/563 B |
| 3,959,374 | 5/1976 | Brennan et al. | 260/563 B |
| 4,218,308 | 8/1980 | Itoh et al. | 502/261 |
| 4,384,142 | 5/1983 | Merten et al. | 564/451 |
| 4,394,522 | 7/1983 | Allen | 564/451 |
| 4,394,523 | 7/1983 | Allen | 564/451 |
| 4,448,995 | 5/1984 | Allen | 564/451 |
| 4,497,909 | 2/1985 | Itoh et al. | 502/262 |
| 4,503,249 | 3/1985 | Nowack et al. | 564/450 |
| 4,591,635 | 5/1986 | Greve et al. | 534/612 |
| 4,754,070 | 6/1988 | Casey et al. | 564/451 |
| 4,946,998 | 8/1990 | Casey et al. | 564/451 |
| 4,952,549 | 8/1990 | Immel et al. | 564/450 |
| 4,960,941 | 10/1990 | Vedage et al. | 564/450 |
| 5,023,226 | 6/1991 | Immel et al. | 564/450 |

FOREIGN PATENT DOCUMENTS 1122609  8/1968  United Kingdom .

OTHER PUBLICATIONS

J. B. Montgomery, A. N. Hoffman, A. L. Glasebrook and J. I. Thigpen, Ind. Eng. Chem. vol. 50, No. 3, (Mar. 1958) pp. 313-316 entitled "Catalytic Perhydrogenation of Rosin".
E. B. Maxted & A. Marsden, Journal Chem. Soc. 469 (1940).
E. B. Maxted & R. W. D. Morrish, Journal Chem. Soc. 252 (1940) 132 (1941).
P. N. Rylander et al., Ind. Tech. Bull., 8, 93 (1967).
R. N. Rylander, J. Kaplan Engelhard, Ind. Tech. Bull., 2, 48 (1961).
D. Rose and C. J. N. Tyrrell, "Preparation of Tris-Oxato Iridates" Engelhard Tech. Bull. Dec. 1967 vol. VIII, No. 3, pp. 99-100.

Primary Examiner—Richard L. Raymond
Assistant Examiner—Scott C. Rand
Attorney, Agent, or Firm—A. A. Meyer, Jr.; F. A. Iskander

[57] ABSTRACT

A process for increasing the rate of catalytic hydrogenation of aromatic amines by reacting aromatic amines with hydrogen in the presence of a noble metal catalyst, an organic solvent or a mixture of solvents, and at least one salt of a transition or lanthanide metal as a promoter, in an effective amount to increase the rate of the hydrogenation reaction, decrease the induction period, and decrease the amount of higher boiler by-products.

13 Claims, No Drawings

PROMOTERS FOR HYDROGENATION OF AROMATIC AMINES

FIELD OF THE INVENTION

This invention relates to a process using transition or lanthanide metal salt promoters in the catalytic hydrogenation of aromatic amines to produce their cycloaliphatic counterparts.

BACKGROUND OF THE INVENTION

Substantial literature exists with respect to the catalytic hydrogenation of aromatic amines to prepare the corresponding cycloaliphatic amines. Illustrative of this type of reaction is the hydrogenation of methylenedianiline 4,4'-diaminodiphenylmethane, MDA] to the cycloaliphatic amine which is bis(4-aminocyclohexyl)methane, also called PACM, $H_{12}$MDA.

The hydrogenation follows a step-wise reaction sequence, giving first the half hydrogenated cis and trans isomers [p-(4-aminocyclohexylmethyl)aniline, 4-(p-aminobenzyl)aminocyclohexane, $H_6$MDA], then reacting further to yield the three bis(4-aminocyclohexyl)methane isomers (cis, cis; cis, trans; and trans, trans) represented by the formulas and reactions as follows:

2,606,928. Basically the processes described in these patents involve the hydrogenation of methylenedianiline at pressures in excess of 200 psig, preferably in excess of 1,000 psig at temperatures within a range of 80° to 275° C. utilizing a ruthenium catalyst for the hydrogenation. The hydrogenation is carried out under liquid phase conditions and an inert organic solvent is used. Most of the references utilize a noble metal such as ruthenium, rhodium, iridium, or mixtures of any of these or with platinum or palladium, either as the hydroxide, oxide, or the metal itself on an inert support. Examples of ruthenium catalysts utilized for the hydrogenation process include ruthenium oxides, such as ruthenium sesquioxide and ruthenium dioxide; ruthenium hydroxide; and ruthenium salts.

U.S. Pat. No. 3,959,374 discloses a process for the preparation of bis(4-aminocyclohexyl)methane by pretreating a mixed methylenedianiline system with a nickel-containing hydrogenation catalyst prior to hydrogenation with ruthenium. The pretreatment was used to overcome low yields (52.4%) and long reaction time associated with nickel and cobalt catalysts. Ruthenium catalysts, although commonly used for hydrogenation, were not suited for hydrogenation of a feed containing impurities. Impurities in the feed caused a rapid decline

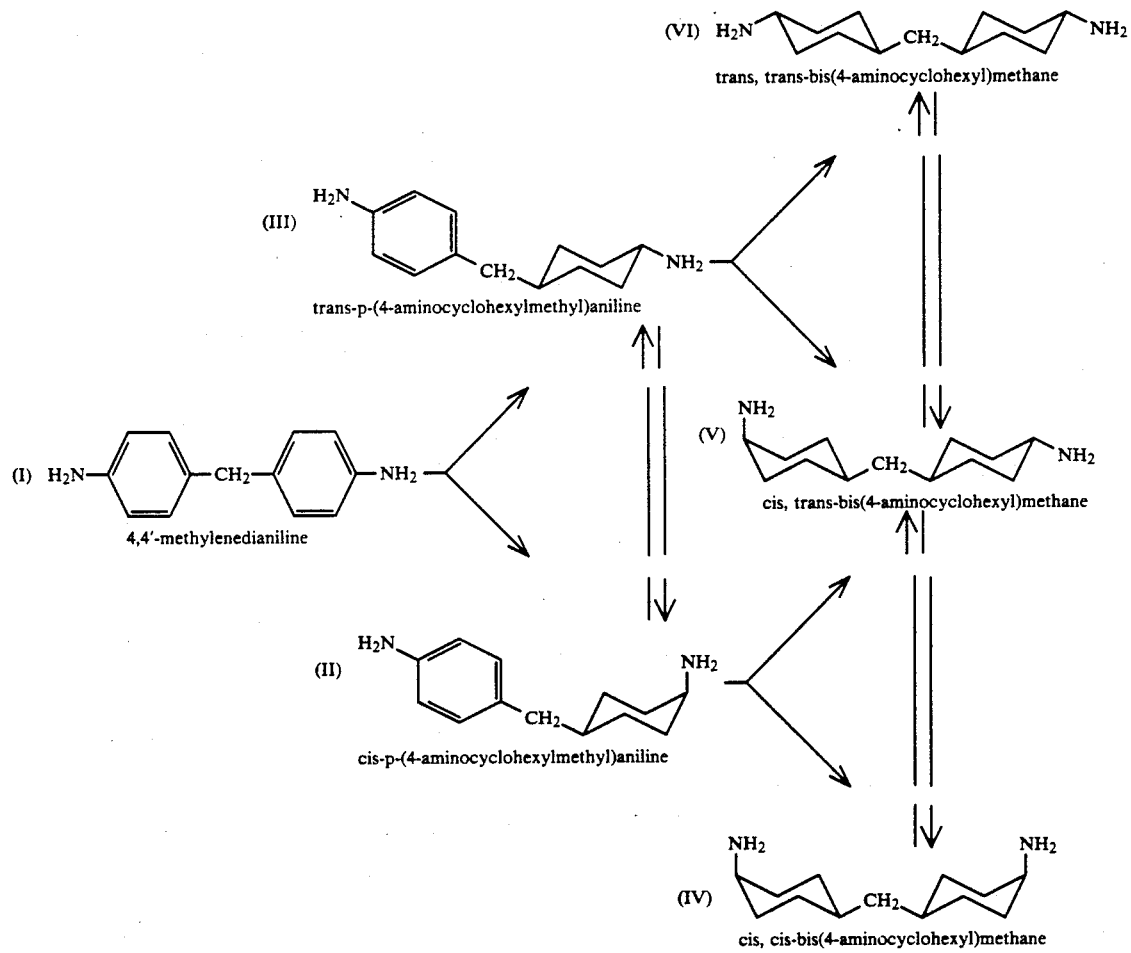

Some of the early hydrogenation work to produce bis(4-aminocyclohexyl)methanes was done by Whitman and Barkdoll, et al and their work is set forth in a series of U.S. Pat. Nos. 2,511,028; 2,606,924; 2,606,925; and in activity and hydrogenation efficiency.

In the continued development of processes for manufacturing bis(4-aminocyclohexyl)methanes by hydrogenating methylenedianiline it was found that if the ruthenium was loaded upon a support and the support was alkali-moderated, the catalyst was much more active and catalytically effective in producing the desired hydrogenated bis(4-aminocyclohexyl)methane product. Alkali moderation was effected by contacting the catalyst with an alkali metal hydroxide or alkoxide; also, such alkali moderation of the catalyst could be effected prior to hydrogenation or in situ during the hydrogenation. Representative patents showing the utilization of alkali moderated ruthenium catalysts to hydrogenate methylenedianiline include U.S. Pat. Nos. 3,636,108; 3,644,522; and 3,697,449. Alkali metal and alkaline earth metal nitrates and sulfates have similarly been shown effective in U.S. Pat. No. 4,448,995 under high pressure (4000 psig) hydrogenation conditions. Representative supports disclosed in U.S. Pat. No. 3,697,449 include bauxite, periclase, zirconia, titania, diatomaceous earth, etc.

U.S. Pat. Nos. 3,347,917; 3,711,550; 3,679,746; 3,155,724; 3,766,272 and British Pat. No. 1,122,609 disclose various isomerization and hydrogenation processes to produce bis(4-aminocyclohexyl)methane containing a high trans,trans-isomer content; i.e. an isomer content near equilibrium typically 50% trans,trans, 43% cis,trans and 7% cis,cis. Ruthenium catalysts were used to effect isomerization.

In U.S. Pat. Nos. 4,394,522 and 4,394,523, a process is disclosed for producing bis(4-aminocyclohexyl)methane by carrying out the hydrogenation of methylenedianiline in the presence of unsupported ruthenium dioxide at pressures of at least 2500 psig or in the presence of ruthenium on alumina under pressures of at least 500 psig and preferably from 1500 psig to 4000 psig in the presence of an aliphatic alcohol and ammonia. Other catalysts have been utilized for the hydrogenation of methylenedianiline and examples are shown in U.S. Pat. Nos. 3,591,635 and 3,856,862 which disclose the use of a rhodium component as a catalytic material and each require the use of an alcohol as a solvent. The rhodium is alkali moderated using ammonium hydroxide as a pretreatment or by carrying out the reaction in the presence of ammonia.

The isomeric cycloaliphatic diamines are useful in the preparation of the corresponding aliphatic diisocyanates suitable for forming light stable urethane coatings and lacquers. In earlier experiments involving the hydrogenation of aniline, it was shown that addition of ammonia not only suppresses by-product formation mainly from hydrogenolysis and condensation reactions, but also poisons the catalyst. However, addition of lithium hydroxide and sometimes sodium hydroxide suppresses the hydrogenolysis without the detrimental poisoning of the catalyst. A similar phenomenon has been reported with the hydrogenation of methylenedianiline using lithium hydroxide, and to a lesser extent, with other alkali or alkaline earth hydroxides or alkoxides. Common by-products formed during the hydrogenation of methylenedianiline include the hydrogenolysis products 4-aminodicyclohexylmethane and 4-aminocyclohexylcyclohexenylmethane, the hydrolysis product 4-amino-4'-hydroxydicyclohexylmethane, and higher boilers, mainly, but not exclusively, higher molecular weight secondary amine condensation products. All of these products exist as a number of isomers.

U.S. Pat. No. 4,448,995 teaches that this hydrogenation reaction should be maintained in an anhydrous state or at least maintained so that water concentration is less than 0.5% by weight because failure to do so results in an increase in both the amount of alcohol by-products and higher molecular weight condensation products. In addition, the patent states that alkali nitrates and sulfates, especially those of lithium reduce by-products.

In some comparisons, the presence of lithium hydroxide has been shown to actually result in an increase in the production of higher molecular weight products. (See U.S. Pat. No. 4,946,998.)

The use of platinum group metals to catalyze hydrogenation reactions is known in the art. Because of the high cost of these catalysts, any method for increasing the activity and/or life of the catalysts is desirable and valuable. The use of lithium hydroxide and related materials for such a purpose has been described above. The search for other promoters (also called activators and moderators) is one method for achieving this goal.

Substances that cause a deactivation of the catalyst are called poisons or inhibitors. The only difference between the two is the amount of loss of catalyst activity. For the purpose of this application, the term catalyst poison will be used in referring to all such phenomena. It has been found, generally, that heavy metals either are detrimental (catalyst poisons) or have no effect on platinum group metal catalysts used in hydrogenation reactions. Specifically, it has been found that Pb, Cu, Ni, Bi, and Cr behave as poisons for Pt in the hydrogenation of nitrobenzene in the preparation of aniline. Ag has been found to poison Pd catalysts in the same reaction. A careful study of the ring hydrogenation of rosin derivatives (not containing an amine) showed that the following metals, introduced as nitrates, functioned as catalyst poisons: Pb, Hg, Zn, Cu, Al, Mn, Ti, Mg, Na, Cr, Ni, and Ca. [J. B. Montgomery, et al., Ind. Eng. Chem., 50, 313 (1958)]. Acetates of the following metals have been disclosed as catalyst poisons: Cu, Ag, Au, Zn, Cd, Hg, Tl, In, Ti, Sn, Pb, Bi, Mn, Fe, Co, and Ni. [E. B. Maxted and A. Marsden, J. Chem. Soc. 469 (1940)].

The poisoning of catalysts is essentially a preferential adsorption effect dependent on the attraction between a catalyst and certain types of adsorbed species which are usually, but not always, foreign to the reacting system to be catalyzed. In most cases, the strong adsorptive bond by means of which the poison is held to the catalyst appears to be of a highly specific and chemical nature, the formation of such bonds being apparently dependent on definite types of electronic configuration both in the catalyst and in the poison. Substances are in practice only regarded as poisons if they exert an appreciable inhibitive effect on the catalysis even when present in very small concentrations. This concept of poisoning does not include the mechanical covering of a catalyst surface by less specifically held coatings, such as the cloaking of a catalyst by a layer of gums or waxes or deposit of carbon in organic reactions at high temperature.

The counter-ion of the metal salt can be chosen from a variety of possibilities. However, many are known to cause poisoning. Species with non-bonded electron pairs are known to be deleterious to catalysts. They become strongly attracted to noble metals and catalyst deactivation results. Monatomic ions that possess non-bonded electrons often, but not always act as catalyst poisons. Ions of this type such as halides are occasionally used as counter-ions, but are not preferable. Many sulfur and phosphorus compounds and their analogs with non-bonded electrons on the sulfur and the phosphorus are among the strongest catalyst poisons. Moieties such as sulfates, phosphates, and their analogs which have no non-bonded electrons around the central atom exhibit no catalyst poisoning. Examples of catalyst poisons and non-poisons are shown below:

Influence of Electronic Configuration on Toxicity

| Toxic types | Nontoxic types (shielded structure) |
|---|---|
| H–S̈–H    H–P̈–H | $\begin{bmatrix} O \\ O-P-O \\ O \end{bmatrix}^{3-}$ |
| Hydrogen sulfide   Phosphine | Phosphate ion |
| $\begin{bmatrix} O \\ O-S̈-O \end{bmatrix}^{2-}$ | $\begin{bmatrix} O \\ O-S-O \\ O \end{bmatrix}^{2-}$ |
| Sulfite ion (also selenite and tellurite) | Sulfate ion (also selenate and tellurate) |
| (R)C–S̈–H | $\begin{array}{c} O \\ (R)C-S-OH \\ O \end{array}$ |
| Organic thiol | Sulfonic acid |
| (R)C–S̈–C(R') | $\begin{array}{c} O \\ (R)C-S-C(R') \\ O \end{array}$ |
| Organic sulfide | Sulfone |

[E. B. Maxted and R. W. D. Morrish, J. Chem. Soc. 252 (1940); 132 (1941)].

Some reduction reactions have induction periods, i.e. a time required before the maximum rate is obtained or before hydrogenation occurs. Ruthenium catalysts are known to be particularly inclined to exhibit induction periods, but this phenomenon has also been observed with other noble metals. In the reduction of aldehydes to alcohols, stannous chloride was shown to be an effective promoter in eliminating the induction period and giving a slight increase in rate. [P. N. Rylander and J. Kaplan, Engelhard Ind. Tech. Bull., 2, 48 (1961); P. N. Rylander, et al., Engelhard Ind. Tech. Bull., 8, 99 (1967).]

In contrast the process of the present invention has found that when a transition and/or lanthanide metal salt is used as a promoter in a catalytic hydrogenation reaction of aromatic amines, there is an increase in the reaction rate, decrease or elimination of the induction period, and a decrease in the amount of the high boiler by-products of the reaction.

SUMMARY OF THE INVENTION

It is an object of the present invention to provide a process for increasing the reaction rate by using a metal salt promoter in the catalytic hydrogenation of aromatic amines to produce their cycloaliphatic counterparts.

It is also another object of the invention to provide a process for decreasing or eliminating the induction period by using a metal salt promoter in the catalytic hydrogenation of aromatic amines to produce their cycloaliphatic counterparts.

Another object of the invention is to increase the reaction rate by using a metal salt promoter in the catalytic hydrogenation of aromatic amines to produce their cycloaliphatic counterparts with a decrease in the amounts of higher boiler by-products.

These and other objects of the invention are accomplished in an improved process for the catalytic hydrogenation of aromatic amines to produce their cycloaliphatic counterparts which process comprises effecting the catalytic hydrogenation in the presence of a noble metal catalyst, an organic solvent for said amine, and a transition and/or lanthanide metal salt promoter.

DETAILED DESCRIPTION OF THE INVENTION

The present invention relates to a process for increasing the rate of conventional ring hydrogenation of aromatic amines to their cycloaliphatic counterparts and these aromatic amines are represented by the formula:

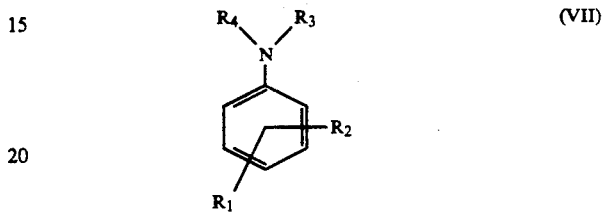

(VII)

in which $R_1$ is selected from the group consisting of H, an alkyl or cycloalkyl group having 1–6 carbon atoms, and $NH_2$;

$R_2$ is selected from the group consisting of H, an alkyl or cycloalkyl group having 1–6 carbon atoms, and

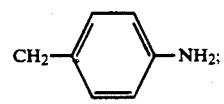

and $R_3$ and $R_4$ are independently selected from the group consisting of H, and an alkyl or cycloalkyl group having 1–6 carbon atoms.

By the practice of this invention, one is able to increase the rate of hydrogenation of aromatic amines to their cycloaliphatic counterparts, decrease or eliminate the induction period, and decrease the amounts of higher boiler by-products formed during reaction. The aromatic amines useful in the practice of the process can be bridged polynuclear or mononuclear aromatic amines. These can be substituted with various substituents such as an alkyl group or cycloalkyl group containing from 1–6 carbon atoms. Further, the amine group can be substituted with alkyl or cycloalkyl groups having 1–6 carbon atoms resulting in secondary and tertiary amine substituents. Examples of bridged aromatic amines include methylenedianiline ($R_1$ is H and $R_2$ is

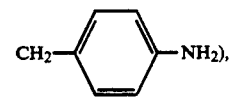

bis(4-amino-2-methylphenyl)methane, tolidine, and alkyl or cycloalkyl secondary and tertiary amine derivatives of above bridged aromatic amines. Examples of mononuclear aromatic amines include 2,4- and 2,6-toluenediamine, aniline, 1-methyl-3,5-diethyl-2,4- or 2,6-diaminobenzene (diethyltoluenediamine), diisopropyltoluenediamine, tert-butyl-2,4- or 2,6-toluenediamine, cyclopentyltoluenediamine, ortho-toluidine, ethyltoluidine, xylenediamine, mesitylenediamine, mono-isopropyltoluenediamine, phenylenediamine, and alkyl and cycloalkyl secondary and tertiary amine derivatives of the aromatic amines mentioned above.

As with conventional processes the hydrogenation process is carried out under liquid phase conditions being maintained typically by carrying out the hydrogenation in the presence of a solvent. Any solvent or solvent mixture that dissolves and is inert to the reactant and product, should be equally usable. Representative solvents suitable for practicing the invention include low molecular weight alcohols, such as methanol, ethanol, isopropanol, tert-butyl alcohol and methoxyethanol; and low molecular weight aliphatic and alicyclic hydrocarbon ethers, such as n-propyl ether, isopropyl ether, glyme, tetrahydrofuran, and dioxane. Dioxane is preferred. A mixed solvent system may also be used such as an alcohol or an ether mixed together, or either of these with another solvent such as a hydrocarbon or water.

A noble metal catalyst such as ruthenium, rhodium, iridium, or mixtures of any of these or with platinum or palladium, either as the hydroxide, oxide or, the metal itself on an inert support may be utilized for the hydrogenation process. The catalysts used are supported upon an inert carrier and representative carriers include carbon; calcium carbonate; rare earth oxides such as cerium, praseodymium, or lanthanum; rare earth carbonates; alumina; barium sulfate; kieselguhr; pumice; titania; diatomaceous earth; and other alkaline earth compounds such as calcium sulfate, calcium oxide, barium oxide, and barium sulfate. preferred support material is alumina. The preferred catalyst is ruthenium on alumina carrier (Ru/Al$_2$O$_3$). A 5% ruthenium on alumina loading, a commercial product available from the Aldrich Chemical Co., is illustrative, but any percent loading can be utilized.

To maintain high activity of the catalyst system in the hydrogenation process, a transition and/or lanthanide metal salt promoter is added to the reaction system in an effective amount to increase the hydrogenation rate, eliminate the induction period of the hydrogenation reaction, and decrease the amount of higher boiler by-products and thus, the term "effective amount" is intended to include any such amount which accomplishes this. By way of illustration, an effective amount of the transition or lanthanide metal salt promoter is in the range from about 0.1% to about 15% by weight based on the starting aromatic amine. Preferred range is from about 0.3% to about 10.0%. These metal salt promoters can be used alone or in combination with other additives.

The transition metal salts that can be used according to the invention are salts of the following transition metals: Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, and Hg. Preferred salts are those of the metals: Sc, Ti, Cr, Mn, Fe, Co, Ni, Cu, Zn, Zr, Mo, Ru, and Hf. Most preferred is Fe.

The lanthanide metal salts that can be used according to the invention are salts of the following lanthanide metals: La, Ce, Pr, Nd, Pm, Sm, Eu, Gd, Tb, Dy, Ho, Er, Tm, Yb, and Lu. Preferred metal salts are those of La, Ce, Pr, Nd, Sm, Tb, Er, and Yb. Most preferred are metal salts of La and Ce.

Counter-ions such as the sulfate and phosphate can be used because they do not have non-bonded electrons on the sulfur and phosphorus respectively. Thus, ferrous and cerous sulfates (either as the anhydrous salt or as a hydrate) are illustrative. Other anions that satisfy these criteria such as carboxylates (e.g. acetates) can be used.

Promoters of the invention are used to enhance the reaction by decreasing by-products, increasing the reaction rate, and decreasing or eliminating the induction period in the hydrogenation reaction.

The reaction can be carried out at any suitable temperature range, preferably from about 80° C. to about 240° C. In the case of methylenedianiline, the optimum temperature is dependent on the desired bis(4-aminocyclohexyl)methane isomer ratio. In order to achieve a 20% trans, trans content or less the lower end of the temperature range is desirable. To achieve a 48% trans,-trans content, this reaction must take place in the mid-range or above 170° C.

Also the reaction may be operated at any suitable pressure, preferably from about 500 to about 4000 psig with the most preferred range from about 1000 to about 3000 psig.

The concentration of starting aromatic amine in solution can vary from 1% to neat (without solvent), preferably from 3% to 50% are utilized.

The progress of the hydrogenation reaction is followed readily by observation of the amount of hydrogen taken up by the reaction mixture and the hydrogenation is terminated at the point at which the theoretical quantity of hydrogen has been consumed. Following the hydrogenation, the catalyst can be filtered through celite and can be optionally reused. The solvent is distilled and also can be optionally reused. The residual cycloaliphatic amine can be either used as is, or purified by vacuum distillation or crystallization.

The promoters of the invention can be used in the hydrogenation of any aromatic amine. The hydrogenation of methylenedianiline is used to demonstrate the invention.

The following examples are presented to further illustrate the invention without any intention of being limited thereby. All parts and percentages are by weight unless otherwise specified except for percent yield which is mole percent.

EXAMPLE 1

In a 600 ml Parr pressure reactor, the following were added: 3.0 g of methylenedianiline, 0.20 g of 5% ruthenium on alumina, 0.15 g of ferrous sulfate heptahydrate (promoter) and 95 g of dioxane. The reactor was flushed with hydrogen and pressurized. The reaction mixture was heated to 125° C. for 6 hours at 1500 psig. Essentially no induction period was observed. After cooling and release of pressure, the reaction mixture was filtered through celite and evaporated to dryness under aspirator vacuum to give a crude mixture of 0.1% methylenedianiline, 10.8% p-(4-aminocyclohexylmethyl)aniline and 87.2% bis(4-aminocyclohexyl)methane. Only 0.1% higher boilers were obtained.

EXAMPLE 2

The same reaction conditions were utilized as in Example 1, except that 0.06 g of cerous sulfate octahydrate was added. The reaction showed no induction period, and gave essentially no methylenedianiline, 11.4% p-(4-aminocyclohexylmethyl)aniline, and 84.3% bis(4- aminocyclohexyl)methane. No higher boilers were observed.

EXAMPLE 3

The same reaction conditions were utilized as in Example 1, except that 0.15 g of ferrous sulfate heptahydrate and 0.06 g of cerous sulfate octahydrate were added. The reaction showed no induction period and gave essentially no methylenedianiline, 8.3% p-(4-aminocyclohexyl)aniline, and 89.4% bis(4-aminocyclohexyl)methane. No higher boilers were observed.

EXAMPLE 4

In a 600 ml Parr pressure reactor, the following were added: 3.0 g of methylenedianiline, 0.20 g of 5% ruthenium on alumina, and 95 g of dioxane. The reactor was flushed with hydrogen and pressurized. The reaction mixture was heated to 125° C. for 6 hours at 1500 psig. An induction period of approximately one hour was observed. After cooling and release of pressure, the reaction mixture was filtered through celite and evaporated to dryness under aspirator vacuum to give a crude mixture of essentially no methylenedianiline, 17.6% p-(4-aminocyclohexylmethyl)aniline, and 79.5% bis(4-aminocyclohexyl)methane. Approximately 1.4% higher boilers was observed.

EXAMPLE 5

The same reaction conditions were utilized as in Example 4 except that 0.15 g of stannous chloride dihydrate was added. Essentially no hydrogenation took place; only methylenedianiline starting material was observed.

EXAMPLE 6

The same reaction conditions were utilized as in Example 4 except that 0.01 g of stannous chloride dihydrate was added. Essentially no hydrogenation took place; only methylenedianiline starting material was observed.

Examples 1–3 demonstrate an increase in the reaction rate, a decrease or elimination of the induction period, and a decrease of the amount of higher boiler by-products as compared to Example 4. These results were unexpected. Examples 5 and 6 show the effect of catalyst poisoning.

Operable and preferred ranges of reaction conditions are presented in the following table:

TABLE 1

| Variable | Range Operable | Preferred |
|---|---|---|
| Temperature | 80°–240° C. | (1) |
| Pressure | 500–4000 psig | 1000–3000 psig |
| Solvents Concentrations | (2) | (2) |
| MDA: | 1% to neat | 3–50% |
| catalyst: | 0.005–1.0% (3) | 0.05–0.5% (3) |
| promoter: | 0.1–15.0% (4) | 0.3–10.0% (4) |

(1) The "preferred" temperature depends on the desired trans, trans isomer content of the bis(4-aminocyclohexyl)methane. Lower temperatures give a lower (approximate 20% trans, trans) content; increasing the temperature results in a higher (approximate 48% trans, trans) content.
(2) Any organic solvent inert to the starting and product amines and inert to the reaction conditions is usable. Examples include other ethers such as dioxane, glymes, tetrahydrofuran, etc., and alcohols (low molecular weight alcohols, diols, alkoxyalcohols); and dioxane is preferred. A solvent system comprising an alcohol or an ether mixed together or with another solvent such as a hydrocarbon or water may be used.
(3) Based on weight of noble metal to weight of starting amine.
(4) Based on weight of promoter to weight of starting amine.

While the specific invention has been described above with reference to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A process for the catalytic hydrogenation of an aromatic amine represented by the formula:

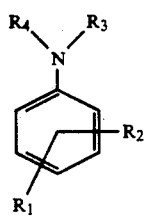

in which:
$R_1$ is selected from the group consisting of H, an alkyl or cycloalkyl group having 1–6 carbon atoms, and $NH_2$;
$R_2$ is selected from the group consisting of H, an alkyl or cycloalkyl group having 1–6 carbon atoms, and

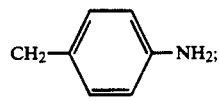

and
$R_3$ and $R_4$ are independently selected from the group consisting of H, and an alkyl or cycloalkyl group having 1–6 carbon atoms;
which process comprises reacting said aromatic amine with hydrogen in a reaction mixture containing an organic solvent, a noble metal catalyst and a promoter admixed with said reaction mixture, said promoter being a metal salt selected from the group consisting of a sulfate, a phosphate and a carboxylate, wherein the metal is selected from the group consisting of transition metals Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, and Hg, and lanthanide metals, said promoter being used in an effective amount to increase the rate of said hydrogenation reaction, decrease the induction period, and decrease the amount of high boiler by-products.

2. The process of claim 1 in which the lanthanide metal is selected from the group consisting of La, Ce, Pr, Nd, Pm, Sm, Eu, Gd, Tb, Dy, Ho, Er, Tm, Yb, and Lu.

3. The process of claim 2 in which the transition metal is selected from the group consisting of Sc, Ti, Cr, Mn, Fe, Co, Ni, Cu, Zn, Zr, Mo, Ru, and Hf, and the lanthanide metal is selected from the group consisting of La, Ce, Pr, Nd, Sm, Tb, Er, and Yb.

4. The process of claim 1 in which at least one promoter is present in an amount from about 0.1% to about 15.0% by weight of the aromatic amine.

5. The process of claim 3 in which the transition metal is Fe, and the lanthanide metal is Ce.

6. The process of claim 5 in which said promoter is selected from the group consisting of ferrous sulfate in the anhydrous or hydrated from, cerous sulfate in the anhydrous or hydrated form and mixtures thereof.

7. The process of claim 6 in which at least one promoter is present in an amount from about 0.3% to about 10.0% by weight of the aromatic amine.

8. A process for the catalytic hydrogenation of methylenedianiline to produce bis(4-aminocyclohexyl)methane, which process comprises reacting said methylenedianiline with hydrogen in a reaction mixture containing an organic solvent, a noble metal catalyst and a metal salt promoter admixed with said reaction mixture, said promoter being selected from the group consisting of a sulfate, a phosphate and a carboxylate, wherein the metal is selected from the group consisting of transition metals Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, and Hg, and lanthanide metals, said promoter being used in an effective amount to increase the rate of said hydrogenation reaction, decrease the induction period, and decrease the amount of high boiler by-products.

9. The process of claim 8 in which the transition metal is selected from the group consisting of Sc, Ti, Cr, Mn, Fe, Co, Ni, Cu, Zn, Zr, Mo, Ru, and Hf, and the lanthanide metal is selected from the group consisting of La, Ce, Pr, Nd, Sm, Tb, Er, and Yb.

10. The process of claim 9 in which at least one promoter is present in an amount from about 0.1% to about 15.0% by weight of the aromatic amine.

11. The process of claim 10 in which the transition metal is Fe and the lanthanide metal is Ce.

12. The process of claim 11 in which said salt is selected from the group consisting of ferrous sulfate in the anhydrous or hydrated form, cerous sulfate in the anhydrous or hydrated from and mixtures thereof.

13. The process of claim 12 in which the promoter is present in an amount from about 0.3% to about 10.0% by weight of the aromatic amine.

* * * * *